United States Patent
Nakashima et al.

(10) Patent No.: US 10,620,177 B2
(45) Date of Patent: Apr. 14, 2020

(54) PROTEIN ADSORPTION INHIBITOR AND METHOD FOR INHIBITING PROTEIN ADSORPTION

(71) Applicant: NOF CORPORATION, Tokyo (JP)

(72) Inventors: Fumio Nakashima, Kawasaki (JP); Satoshi Yamada, Kawasaki (JP); Tomozumi Noda, Kawasaki (JP); Masaru Matsuda, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 418 days.

(21) Appl. No.: 15/509,617

(22) PCT Filed: Sep. 8, 2015

(86) PCT No.: PCT/JP2015/075415
§ 371 (c)(1),
(2) Date: Mar. 8, 2017

(87) PCT Pub. No.: WO2016/039319
PCT Pub. Date: Mar. 17, 2016

(65) Prior Publication Data
US 2017/0261481 A1 Sep. 14, 2017

(30) Foreign Application Priority Data
Sep. 10, 2014 (JP) .................. 2014-184550

(51) Int. Cl.
*G01N 33/15* (2006.01)
*C07F 9/09* (2006.01)
*C07F 9/10* (2006.01)

(52) U.S. Cl.
CPC ............. *G01N 33/15* (2013.01); *C07F 9/091* (2013.01); *C07F 9/10* (2013.01)

(58) Field of Classification Search
CPC ...................................... G01N 33/15
See application file for complete search history.

(56) References Cited

U.S. PATENT DOCUMENTS 6,828,029 B1 * 12/2004 Lewis .................. C08G 77/395
427/384
9,295,747 B2 * 3/2016 Matsuoka ............... A61L 12/10
(Continued)

FOREIGN PATENT DOCUMENTS

EP          3178927 A1    6/2017
JP          04-009665 A    1/1992
(Continued)

OTHER PUBLICATIONS

Matsuno et al. Simple Synthesis of a Library of Zwitterionic Surfactants via Michael-Type Addition of Metharcylate and Alkane Thiol Compounds. Langmuir, Aug. 17, 2010. vol. 26, No. 16 pp. 13028-13035 (Year: 2010).*
(Continued)

*Primary Examiner* — Cachet I Proctor
(74) *Attorney, Agent, or Firm* — Sughrue Mion, PLLC

(57) ABSTRACT

A protein adsorption inhibitor includes a compound of Formula (1) as an active ingredient. The protein adsorption inhibitor is capable of highly inhibiting non-specific adsorption of a protein such as an antibody or an enzyme to a surface of a base body such as an immune reaction vessel or an assay instrument. Also provided is a coating layer-formed base body having a coating layer containing the protein adsorption inhibitor on the base body. The coating layer-formed base body has an excellent protein adsorption-inhibiting function. A method for inhibiting the adsorption of the protein to the base body is provided. The method includes forming the coating layer containing the protein adsorption inhibitor on the surface of the base body:
(Continued)

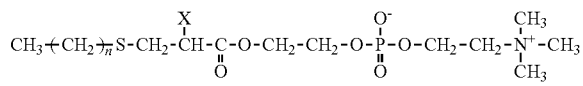

(1)

wherein, X is a hydrogen atom or a methyl group and n is an integer of 9 to 15.

2 Claims, 1 Drawing Sheet

(56) References Cited

U.S. PATENT DOCUMENTS

| | | | |
|---|---|---|---|
| 2003/0212395 A1* | 11/2003 | Woloszko | A61B 18/148 606/41 |
| 2004/0084312 A1* | 5/2004 | Warner | G01N 27/44752 204/454 |
| 2005/0010205 A1* | 1/2005 | Hovda | A61B 18/1482 606/41 |
| 2005/0068543 A1* | 3/2005 | Angeley | G01D 5/35303 356/521 |
| 2009/0130776 A1 | 5/2009 | Imamura et al. | |
| 2010/0298208 A1* | 11/2010 | Cohen | A61K 31/545 514/2.5 |
| 2013/0022621 A1* | 1/2013 | Liu | A61K 39/39591 424/172.1 |
| 2013/0310591 A1* | 11/2013 | Yoshioka | C07F 9/106 558/145 |
| 2015/0148882 A1* | 5/2015 | Ma | A61F 2/82 623/1.2 |
| 2017/0226499 A1 | 8/2017 | Nakashima et al. | |

FOREIGN PATENT DOCUMENTS

| | | |
|---|---|---|
| JP | 04-019561 A | 1/1992 |
| JP | 05-312807 A | 11/1993 |
| JP | 07-083923 A | 3/1995 |
| JP | 2005300313 A | 10/2005 |
| JP | 2007-091736 A | 4/2007 |
| JP | 2011-153101 A | 8/2011 |
| JP | 2012229180 A | 11/2012 |

OTHER PUBLICATIONS

Matsuno et al. Simple Synthesis of a Library of Zwitterionic Surfactants via Michael Type Addition of Methacrylate and Alkane Thiol Compounds. Langmuir Letter. 2010. 26(16) pp. 13028-13032 (Year: 2010).*

Goda et al. Thiolated 2-methacryloyloxyethyl phosphorylcholine for an antifouling biosensor platform. Chem. Commun., 2013. 49. pp. 8683-8685 (Year: 2013).*

European Patent Office, Communication dated Mar. 9, 2018, issued in counterpart European Application No. 15840489.7.

International Bureau, International Preliminary Report on Patentability with a Translation of Written Opinion, dated Mar. 23, 2017, issued in counterpart International Application No. PCT/JP2015/075415.

Tanaka, M. et al., "Synthesis of phosphorylcholine-oligoethylene glycol-alkane thiols and their suppressive effect on non-specific adsorption of proteins", Tetrahedron Letters, 2009, vol. 50, No. 28, pp. 4092-4095.

Chung et al., "The surface modification of silver nanoparticles by phosphoryl disulfides for improved biocompatibility and intracellular uptake", Biomaterials, 2008, vol. 29, No. 12, pp. 1807-1816.

Shengfu Chen et al., "Strong Resistance of Phosphorylcholine Self-Assembled Monolayers to Protein Adsorption: Insights into Nonfouling Properties of Zwitterionic Materials", Journal of the American Chemical Society, 2005, vol. 127, No. 41, pp. 14473-14478.

Ryosuke Matsuno et al., "Simple Synthesis of a Library of Zwitterionic Surfactants via Michael-Type Addition of Methacrylate and Alkane Thiol Compounds", Langmuir Letter, Jul. 16, 2010, pp. 13028-13032, vol. 26, No. 16.

International Searching Authority, International Search Report of PCT/JP2015/075415 dated Dec. 15, 2015.

* cited by examiner

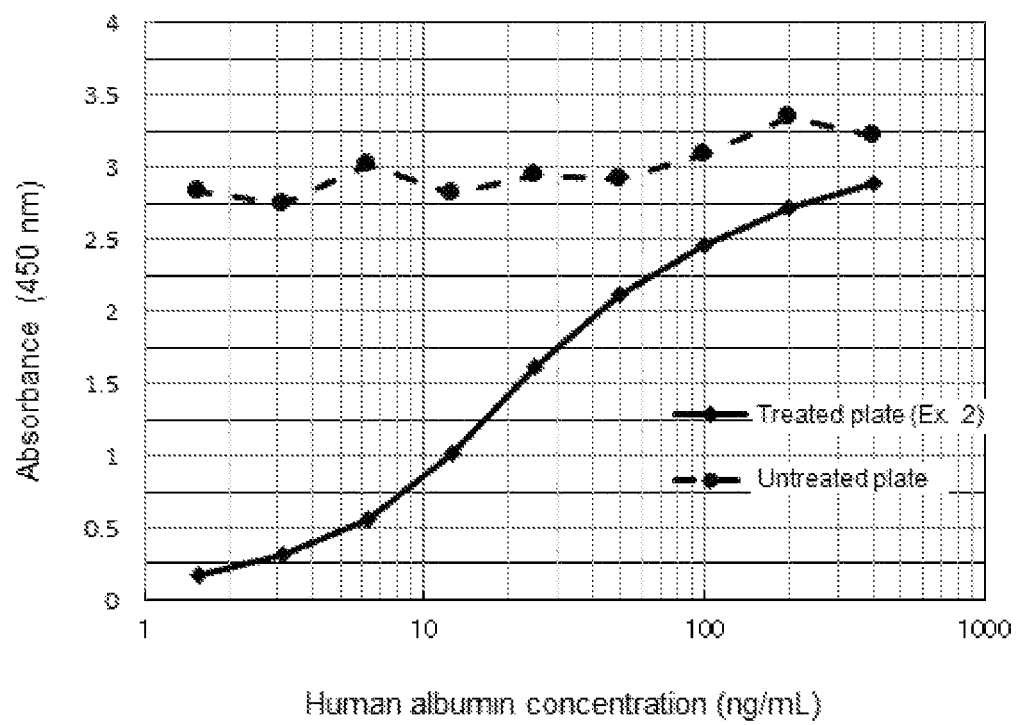

PROTEIN ADSORPTION INHIBITOR AND METHOD FOR INHIBITING PROTEIN ADSORPTION

CROSS REFERENCE TO RELATED APPLICATIONS

This application is a National Stage of International Application No. PCT/JP2015/075415, filed Sep. 8, 2015, claiming priority based on Japanese Patent Application No. 2014-184550, filed Sep. 10, 2014, the contents of all of which are incorporated herein by reference in their entirety.

FIELD OF ART

The present invention relates to inhibition of non-specific protein adsorption. More specifically, the present invention relates to a protein adsorption inhibitor for a diagnostic pharmaceutical, which is used for preventing adsorption or the like of an impurity (a protein) in a sample to a solid phase surface of a base body such as an immune reaction vessel or an assay instrument, and relates to a coating layer-formed base body prepared by treating the base body with the inhibitor. The present invention further relates to a method using the protein adsorption inhibitor for inhibiting the protein adsorption.

BACKGROUND ART

Assay methods utilizing immune responses have been widely used for early disease detection in the fields of clinical examinations and diagnostic pharmaceuticals. The assay methods are desired to have higher detection sensitivities. Thus, there is a great demand for increasing the sensitivities of the clinical examinations and diagnostic pharmaceuticals. In view of the sensitivity increase, assay methods utilizing fluorescence or chemiluminescence are becoming widely used instead of assay methods utilizing reactions of enzymes such as peroxidases and alkaline phosphatases. The assay methods utilizing the fluorescence or chemiluminescence are believed to be capable of detecting the presence of only one molecule of a detection subject substance theoretically. However, in practice, such a desired sensitivity has not been achieved in the methods.

In the assay method utilizing the immune response, the detection sensitivity depends on several factors. The factors include non-specific adsorption of a detection subject such as an antibody or an antigen. or a labeled substance thereof for the assay to a solid phase surface of a base body such as an immune reaction vessel or an assay instrument. In addition, in the case of using a sample containing a plurality of biomolecules such as a serum, a plasma, a cell extract, or a urine, the detection sensitivity may be deteriorated due to noise generated by non-specifc adsorption of various unspecified coexisting substances such as proteins to the solid phase surface of the base body.

In a conventional method for preventing the non-specific adsorption, a biological protein not participating in the immune response, such as a bovine serum albumin, a casein, or a gelatin, is adsorbed to the solid phase surface of the base body such as the immune reaction vessel or the assay instrument to inhibit the non-specific protein adsorption. However, the method using the biological protein such as the bovine serum albumin has problems of biotic contamination such as BSE (bovine spongiform encephalopathy) and difference between lots. Furthermore, storage temperature, duration of use, and the like of the biological protein are limited in the method.

Therefore, several protein adsorption inhibitors containing a chemically synthesized product as a main component have been proposed. Patent Publication 1 discloses a method using a polyvinyl alcohol, and Patent Publication 2 discloses a method using a polymer of 2-methacryloyloxyethyl phosphorylcholine. In these methods, the chemically synthesized product is physically adsorbed to the solid phase surface of the base body such as the immune reaction vessel or the assay instrument, to achieve a protein adsorption-inhibiting effect.

Non-Patent Publication 1 describes that a polymer compound having a phosphatidylcholine group can stabilize a protein. However, Non-Patent Publication 1 does not provide any teaching or suggestion of the protein adsorption-inhibiting effect.

CITATION LIST

Patent Publication 1: JP 04-19561 A

Patent Publication 2: JP 07-83923 A

Non-Patent Publication 1: Ryosuke Matsumoto, Kimiaki Takami, Kazuo Ishihara, "Simple Synthesis of a Zwitterionic Surfactants via Michael-Type Addition of Mathacrylate and Alkane Thiol Compounds", Langmuir Letter, Vol. 26, No. 16, p. 13028-13032, Jul. 16, 2010

SUMMARY OF THE INVENTION

Problems to be Solved by the Invention

However, in the methods disclosed in Patent Publications 1 and 2, although the non-specific protein adsorption to the solid phase surface of the base body such as the immune reaction vessel or the assay instrument can be reduced to some extent, the adsorption cannot be satisfactorily inhibited. Furthermore, the polymer described in Patent Publication 2 has a high molecular weight, so that a solution of the polymer has a high viscosity and a poor handling property.

Accordingly, an object of the present invention is to provide a protein adsorption inhibitor containing a chemically synthesized product capable of highly inhibiting non-specific adsorption of protein such as an antibody or an enzyme to a surface of a base body such as an immune reaction vessel or an assay instrument.

Means for Solving the Problem

As a result of intense research in view of the above object, the inventors have found that a compound represented by Formula (1) can be adsorbed effectively to a surface of a base body such as an immune reaction vessel or an assay instrument, and thereby can highly inhibit protein adsorption to this surface. The present invention has been accomplished based on this finding.

According to an aspect of the present invention, there is provided a protein adsorption inhibitor comprising, as an active ingredient, a compound represented by following Formula (1):

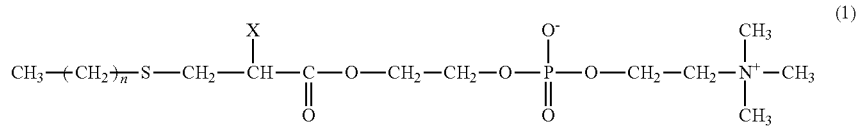

wherein X is a hydrogen atom or a methyl group and n is an integer of 9 to 15.

According to another aspect of the present invention, there is provided a coating layer-formed base body comprising a base body and a coating layer formed on a surface of the base body, wherein the coating layer contains the protein adsorption inhibitor of the present invention.

According to a further aspect of the present invention, there is provided use of the compound represented by Formula (1) for inhibiting adsorption of a protein to a surface of a base body.

According to a still further aspect of the present invention, there is provided a method for inhibiting adsorption of a protein to a base body, comprising treating a surface of the base body with the protein adsorption inhibitor of the present invention to form a coating layer.

Effect of the Invention

The compound of Formula (1), which is used as the active ingredient in the protein adsorption inhibitor of the present invention, can be adsorbed effectively to the surface of the base body such as the immune reaction vessel or the assay instrument, and thereby can highly inhibit the adsorption of the protein to the surface of the base body. Thus, the compound of Formula (1) exhibits a high protein adsorption-inhibiting function. Conventional protein adsorption inhibitors containing biological proteins have problems of difference between lots and biotic contamination. In contrast, the compound of Formula (1) is a chemically synthesized product and thereby can inhibit the protein adsorption safely and reliably without the problems. In addition, the compound of Formula (1) has a low molecular weight and thereby can provide a protein adsorption inhibitor solution with an excellent handling property without excessive viscosity increase.

BRIEF DESCRIPTION OF THE DRAWING

FIG. 1 is a diagram for demonstrating a protein adsorption-inhibiting effect of a coating layer-formed base body according to Example 2, which has a coating layer containing a protein adsorption inhibitor on a surface of a base body.

EMBODIMENTS OF THE INVENTION

The present invention will be described in more detail below.

The protein adsorption inhibitor of the present invention can be used in an immunoassay or the like utilizing an enzyme reaction or an antigen-antibody reaction. For example, a protein, a polypeptide, a steroid, a lipid, a hormone, or the like, i.e. an antigen, an antibody, a receptor, an enzyme, or the like, is used in the reaction. More specifically, the protein adsorption inhibitor can be used in known radioimmunoassay (RIA), enzyme immunoassay (ETA), fluorescence immunoassay (FIA), latex turbidimetry, or the like, particularly preferably enzyme immunoassay (FIA), fluorescence immunoassay (FIA), latex turbidimetry, western blotting, or the like. In the immunoassay, for example, an antibody or an antigen is bonded to a surface of a base body, and a portion of the surface, to which the antibody or antigen is not bonded, is treated with the protein adsorption inhibitor of the present invention, to inhibit adsorption of another protein.

In the protein adsorption inhibitor of the present invention, a compound represented by following Formula (1) is used as an active ingredient.

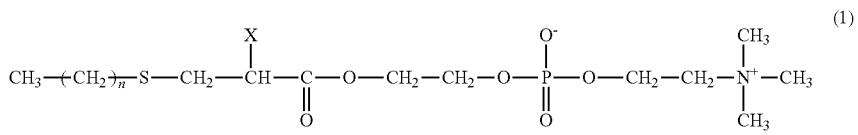

In Formula (1), X is a hydrogen atom or a methyl group, and n is an integer of 9 to 15, preferably an integer of 13 to 15. When n is less than 9, the protein adsorption-inhibiting effect of the compound may be lowered. When n is more than 15, the compound may be hardly soluble in an aqueous solvent.

For example, the compound of Formula (1) may be synthesized by reacting 2-methacryloyloxyethyl-2-trimethylammonioethyl phosphate (MPC) and a 1-alkanethiol with an amine-based catalyst such as diisopropylamine in an alcohol solvent at room temperature for 10 to 50 hours. The 1-alkanethiol preferably has 10 to 16 carbon atoms.

A protein adsorption inhibitor solution may contain another compound in addition to the inhibitor compound represented by Formula (1).

The other compound may be a known compound commonly used in this field, and examples thereof include amino acids such as glycine, alanine, serine, threonine, glutamic acid, aspartic acid, glutamine, asparagine, lysine, and histidine, salts of the amino acids, peptides such as glycylglycine, inorganic salts such as phosphates, borates, sulfates, and Tris salts, organic acids such as flavins, acetic acid, citric acid, malic acid, maleic acid, and gluconic acid, and salts of the organic acids.

In the protein adsorption inhibitor of the present invention, the content of the compound represented by Formula (1) may be 100% by mass. When the content is 50% by mass or more, the compound can exhibit the above effect as the active ingredient.

The protein adsorption inhibitor of the present invention can be preferably dissolved in a solvent, a buffer, or the like, to prepare a protein adsorption inhibitor solution. The solvent may be a water such as a purified water, a pure water, or an ion-exchange water, or an alcohol such as methanol, ethanol, or isopropanol. The buffer is not limited as long as it can be used in an immunoassay, and examples of such buffers include phosphate buffers, acetate buffers, carbonate buffers, citrate buffers, iris buffers, HEPES buffers, and salines. In a case where a surface of a base body is treated with the protein adsorption inhibitor solution according to the present invention to form a coating layer as described hereinafter, it is preferred that the solution contains the water, methanol, ethanol, isopropanol, or a mixture thereof having an arbitrary mixture ratio as the solvent. Also the buffer may be used in this case.

In the protein adsorption inhibitor solution, the content of the compound represented by Formula (1) is preferably 0.01% by mass or more, more preferably 0.1% by mass or more. The upper limit of the content is not particularly limited as long as the compound can be dissolved in the solvent or the buffer. The content is for example 20% by mass or less, preferably 10% by mass or less. When the content is within the range, the protein adsorption inhibitor solution can exhibit a high protein adsorption-inhibiting effect.

The coating layer-formed base body of the present invention, which contains a base body and a coating layer formed on a surface of the base body, will be described below.

The base body used in the present invention is not particularly limited, and examples of materials for the base body include polystyrenes, polyvinyl chlorides, polypropylenes, acrylic resins, polymethyl methacrylates, glasses, metals, ceramics, silicon rubbers, polyvinylidene fluorides (hereinafter referred to as PVD), nylons, and nitrocelluloses. Among them, the polystyrenes and PVDFs are preferred, and the polystyrenes are particularly preferred.

The shape of the base body is not particularly limited. Specific examples of the shapes include membrane shapes, plate shapes, particle shapes, test tube shapes, vial shapes, and flask shapes.

In the formation of the coating layer containing the protein adsorption inhibitor of the present invention on the surface of the base body, for example, the protein adsorption inhibitor of the present invention is dissolved in the solvent such as the water, methanol, ethanol, isopropanol, or a mixture thereof having an arbitrary mixture ratio to prepare the protein adsorption inhibitor solution, the base body is immersed in the protein adsorption inhibitor solution, and the resultant is sufficiently dried at room temperature or a higher temperature to form the coating layer. In the protein adsorption inhibitor solution for forming the coating layer, the concentration of the compound represented by Formula (1) is preferably 0.1% to 5.0% by mass, more preferably 1.0% to 3.0% by mass.

Several methods of using the protein adsorption inhibitor of the present invention will be described below.

In an embodiment, the protein adsorption inhibitor of the present invention is used for forming the coating layer on the surface of the base body as described above, thereby inhibiting adsorption of a protein to the base body in an assay. Thus, the compound represented by Formula (1) is adsorbed in the form of the coating layer to the surface of the base body such as an immune reaction vessel or an assay instrument, whereby the protein is prevented from adsorbing to the surface.

The coating layer containing the protein adsorption inhibitor may be formed on the surface of the base body such as the immune reaction vessel or the assay instrument before the assay. Alternatively, the protein adsorption inhibitor of the present invention may be added to a reagent to be used in the assay. In this method, the coating layer containing the protein adsorption inhibitor may be formed on the base body in a step in the assay. The protein adsorption inhibitor of the present invention may be added to any reagent or solution for the assay other than detection subject samples.

In the reagent or solution used in this method, the concentration of the compound represented by Formula (1) is preferably 0.0125% to 5.0% by mass, more preferably 0.1% to 0.5% by mass.

Incidentally, in a case where the protein adsorption inhibitor is added to the reagent or solution in a step in the assay, the protein adsorption inhibitor is added before the addition of the detection subject sample containing the protein such as a serum, a labeled antibody, or a labeled antigen.

In another embodiment, the protein in the sample such as an enzyme, a labeled antibody, or a labeled antigen is bonded to the surface of the base body such as the immune reaction vessel or the assay instrument, and then the base body is treated with the protein adsorption inhibitor of the present invention. For example, in the case of using a polystyrene plate, the detection subject protein is physically adsorbed or chemically bonded to the plate, the resultant plate is washed with an appropriate solvent, and then the protein adsorption inhibitor solution according to the present invention is brought into contact with the plate. Thus, the detection subject is adsorbed to the surface of the plate, and then the protein adsorption inhibitor of the present invention is adsorbed to a portion of the surface, to which the detection subject is not adsorbed, to inhibit the protein adsorption. Consequently, the coating layer-formed base body having a surface with a protein adsorption-inhibiting effect can be obtained.

Also in this embodiment, the base body may be of an above-described type and may have an above-described shape.

EXAMPLES

The present invention will be described more specifically below with reference to Examples and Comparative Examples without intention of restricting the invention. In Examples, compounds of Formula (1) prepared in Synthesis Examples were used as active ingredients in protein adsorption inhibitors, <Synthesis of Compound Represented by Formula (1)>

Synthesis Example 1

14.7635 g (0.050 mol) of 2-methacryloyloxyethyl-2-trimethylammonioethyl phosphate (MPC) and 9.5893 g (0.055 mol) of 1-decanethiol were dissolved in 81.00 g of ethanol (EtOH). To this was added 0.2226 g (0.0022 moi) of diisopropylamine as a catalyst, and the compounds were reacted at the room temperature for 24 hours. After the reaction, the reaction liquid was concentrated, and the residue was reprecipitated with ethyl acetate to produce a white powder of the compound represented by Formula (1), 2-[3-(decylsulfanyl)-2-methylpropionyloxy]ethyl-2-(trimethylammonio)ethyl phosphate (X is a methyl group and n is 9 in Formula (1)).

Synthesis Example 2

A white powder of the compound represented by Formula (1), 2-[3-(dodecylsulfanyl)-2-methylpropionyloxy]ethyl-2-

(trimethylammonio)ethyl phosphate (X is a methyl group and n is 11 in Formula (1)), was produced in the same manner as Synthesis Example 1 except that 1-dodecanethiol was used instead of 1-decanethiol, and the amount was controlled to obtain the same molar ratio as Synthesis Example 1.

Synthesis Example 3

A white powder of the compound represented by Formula (1), 2-[3-(tetradecylsulfanyl)-2-methylpropionyloxy]ethyl-2-(trimethylammonio)ethyl phosphate (X is a methyl group and n is 13 in Formula (1)), was produced in the same manner as Synthesis Example 1 except that 1-tetradecanethiol was used instead of 1-decanethiol, and the amount was controlled to obtain the same molar ratio as Synthesis Example 1.

Synthesis Example 4

A white powder of the compound represented by Formula (1), 2-[3-(hexadecylsulfanyi)-2-methylpropionyloxy]ethyl-2-(trimethylammonio)ethyl phosphate (X is a methyl group and n is 15 in Formula (1)), was produced in the same manner as Synthesis Example 1 except that 1-hexadecanethiol was used instead of 1-decanethiol, and the amount was controlled to obtain the same molar ratio as Synthesis Example 1.

Comparative Synthesis Example 1

A white powder of the compound represented by Formula (1), 2-[3-(butyisuifanyl)-2-methylpropionyloxy]ethyl-2-(trimethylammonio)ethyl phosphate (X is a methyl group and n is 3 in Formula (1)), was produced in the same manner as Synthesis Example 1 except that 1-butanethiol was used instead of 1-decanethiol, and the amount was controlled to obtain the same molar ratio as Synthesis Example 1.

Comparative Synthesis Example 2

A white powder of the compound represented by Formula (1), 2-[3-(hexylsulfanyl)-2-methylpropionyloxy]ethyl-2-(trimethylammonio)ethyl phosphate (X is a methyl group and n is 5 in Formula (1)), was produced in the same manner as Synthesis Example 1 except that 1-hexanethiol was used instead of 1-decanethiol, and the amount was controlled to obtain the same molar ratio as Synthesis Example 1.

Comparative Synthesis Example 3

A white powder of the compound represented by Formula (1), 2-[3-(octylsulfanyl)-2-methylpropionyloxy]ethyl-2-(trimethylammonio)ethyl phosphate (X is a methyl group and n is 7 in Formula (1)), was produced in the same manner as Synthesis Example 1 except that 1-octanethiol was used instead of 1-decanethiol, and the amount was controlled to obtain the same molar ratio as Synthesis Example 1.

Comparative Synthesis Example 4

A white powder of the compound represented by Formula (1), 2-[3-(eicosasulfanyl)-2-methylpropionyloxy]ethyl-2-(trimethylammonio)ethyl phosphate (X is a methyl group and n is 19 in Formula (1)), was produced in the same manner as Synthesis Example 1 except that 1-eicosanethiol was used instead of 1-decanethiol, and the amount was controlled to obtain the same molar ratio as Synthesis Example 1.

Example 1-1

Examples 1-1-1 to 1-1-4

<Preparation of Protein Adsorption Inhibitor Solution>

The compound of Synthesis Example 1 was dissolved in a Dulbecco's phosphate buffer available from Sigma-Aldrich (hereinafter referred to as the D-PBS) to prepare a protein adsorption inhibitor solution having a concentration of 0.5% to 5% by mass according to each of Examples 1-1-1 to 1-1-4.

<Evaluation of Protein Adsorption-Inhibiting Effect>

The protein adsorption-inhibiting effect of the protein adsorption inhibitor solution was evaluated as follows.

Inc protein adsorption inhibitor solution was added to the polystyrene plate MAXISORP (trademark) available from Thermo Fisher Scientific at 200 µl/well, and left at the room temperature for 2 hours. Then, the solution was completely removed by an aspirator. POD-IgG (peroxidase-labeled immunoglobulin G) available from Biorad was 20000-fold diluted with the D-PBS, and the resultant POD-IgG solution was added to the plate at 100 µl/well and left at the room temperature for 1 hour. Then, the POD-IgG solution was completely removed by the aspirator. A phosphate buffer containing 0.05% by mass of Tween 20 was added to the plate at 200 µL/well, and the solution was removed by the aspirator immediately after the addition. The process of the addition and removal was repeated 5 times to wash the plate surface. After the washing, TMB Microwell Peroxidase Substrate available from KPL was added to the plate at 100 µL/well, and reacted at the room temperature for 7 minutes. A 1-mol/L sulfuric acid solution was added thereto at 50 µL/well to stop the chromogenic reaction, and the absorbance was measured with respect to a light having a wavelength of 450 nm by the microplate reader Spectra Max M3 available from Molecular Devices to detect the adsorbed protein. A lower absorbance means that the protein adsorption was inhibited more highly.

In the evaluation of the protein adsorption-inhibiting effect, the absorbance of an example using a conventional bovine serum albumin was used as a reference. When a protein adsorption inhibitor exhibited an absorbance similar to that of the bovine serum albumin, the inhibitor was judged to have a sufficient effect. The evaluation results are shown in Table 1.

Example 1-2

Examples 1-2-1 to 1-2-6

Protein adsorption inhibitor solutions were prepared in the same manner as Example 1-1 except that the compound produced in Synthesis Example 2 was used instead of the compound produced in Synthesis Example 1 at the concentrations shown in Table 1 respectively. The protein adsorption-inhibiting effects of the solutions were evaluated in the same manner as Example 1-1. The results are shown in Table 1

Example 1-3

Examples 1-3-1 to 1-3-9

Protein adsorption inhibitor solutions were prepared in the same manner as Example 1-i except that the compound produced in Synthesis Example 3 was used instead of the compound produced in Synthesis Example 1 at the concentrations shown in Table 1 respectively. The protein adsorption-inhibiting effects of the solutions were evaluated in the same manner as Example 1-1. The results are shown in Table 1.

Example 1-4

Examples 1-4-1 to 1-4-8

Protein adsorption inhibitor solutions were prepared in the same manner as Example 1-i except that the compound produced in Synthesis Example 4 was used instead of the compound produced in Synthesis Example 1 at the concentrations shown in Table 1 respectively. The protein adsorption-inhibiting effects of the solutions were evaluated in the same manner as Example 1-1. The results are shown in Table 1.

Comparative Example 1-1

The protein adsorption-inhibiting effect of Comparative Example 1-1 was evaluated in the same manner as Example 1-1 except that the protein adsorption inhibitor was not used and only the D-PBS was used. The result is shown in Table 1.

Comparative Example 1-2

The protein adsorption-inhibiting effect of Comparative Example 1-2 was evaluated in the same manner as Example 1-1 except that a bovine serum albumin available from Sigma-Aldrich (hereinafter referred to as the BSA) was used as a protein adsorption inhibitor to prepare a protein adsorption inhibitor solution having a concentration of 2% by mass. The result is shown in Table 1.

Comparative Example 1-3

The protein adsorption-inhibiting effect of Comparative Example 1-3 was evaluated in the same manner as Example 1-1 except that the compound produced in Comparative Synthesis Example 1 was used instead of the compound produced in Synthesis Example 1 at the concentration of 5% by mass. The result is shown in Table 1.

Comparative Example 1-4

The protein adsorption-inhibiting effect of Comparative Example 1-4 was evaluated in the same manner as Example 1-1 except that the compound produced in Comparative Synthesis Example 2 was used instead of the compound produced in Synthesis Example 1 at the concentration of 5% by mass. The result is shown in Table 1.

Comparative Example 1-5

The protein adsorption-inhibiting effect of Comparative Example 1-5 was evaluated in the same manner as Example 1-1 except that the compound produced in Comparative Synthesis Example 3 was used instead of the compound produced in Synthesis Example 1 at the concentration of 5% by mass. The result is shown in Table 1.

Comparative Example 1-6

Preparation of a protein adsorption inhibitor solution was tested in the same manner as Example 1-1 except for using the compound produced in Comparative Synthesis Example 4. However, the compound produced in Comparative Synthesis Example 4 was not dissolved in the D-PBS, so that the protein adsorption-inhibiting effect could not evaluated.

TABLE 1

| | | Protein adsorption inhibitor | | |
|---|---|---|---|---|
| | | Syn. Ex. | Concentration (% by mass)[1] | Absorbance (at 450 nm) |
| Ex. 1-1 | -1 | 1 | 5.00000 | 0.046 |
| | -2 | | 2.00000 | 0.049 |
| | -3 | | 1.00000 | 0.060 |
| | -4 | | 0.50000 | 0.166 |
| Ex. 1-2 | -1 | 2 | 5.00000 | 0.047 |
| | -2 | | 2.00000 | 0.046 |
| | -3 | | 1.00000 | 0.050 |
| | -4 | | 0.50000 | 0.053 |
| | -5 | | 0.20000 | 0.066 |
| | -6 | | 0.10000 | 0.296 |
| Ex. 1-3 | -1 | 3 | 5.00000 | 0.046 |
| | -2 | | 2.00000 | 0.046 |
| | -3 | | 1.00000 | 0.044 |
| | -4 | | 0.50000 | 0.045 |
| | -5 | | 0.20000 | 0.045 |
| | -6 | | 0.10000 | 0.046 |
| | -7 | | 0.02500 | 0.056 |
| | -8 | | 0.01250 | 0.081 |
| | -9 | | 0.00625 | 2.339 |
| Ex. 1-4 | -1 | 4 | 5.00000 | 0.044 |
| | -2 | | 2.00000 | 0.046 |
| | -3 | | 1.00000 | 0.045 |
| | -4 | | 0.50000 | 0.047 |
| | -5 | | 0.20000 | 0.049 |
| | -6 | | 0.10000 | 0.051 |
| | -7 | | 0.01250 | 0.091 |
| | -8 | | 0.00625 | 0.244 |
| Comp. Ex. 1-1 | | — | — | 2.000 |
| Comp. Ex. 1-2 | | BSA[2] | 2.00000 | 0.046 |
| Comp. Ex. 1-3 | | Comp. Syn. Ex. 1 | 5.00000 | 2.123 |
| Comp. Ex. 1-4 | | Comp. Syn. Ex. 2 | 5.00000 | 1.541 |
| Comp. Ex. 1-5 | | Comp. Syn. Ex. 3 | 5.00000 | 0.163 |

[1] Concentration in protein adsorption inhibitor solution
[2] Bovine serum albumin The BSA used in Comparative Example 1-2 is a common biological protein having an excellent protein adsorption-inhibiting function. Each protein adsorption inhibitor according to the present invention contained the compound represented by Formula (1) as the active ingredient, and thereby exhibited a protein adsorption-inhibiting function similar to that of the BSA in contrast, Comparative Examples other than Comparative Example 1-2 exhibited poor protein adsorption-inhibiting functions.

Example 2

<ELISA Test>
[Production of Treated Plate for Evaluating Protein Adsorption-Inhibiting Effect]

Human Albumin Coating Antibody available from. Bethyl Laboratories was 100-fold diluted with Sample/Conjugate Diluent available from Bethyl Laboratories (hereinafter referred to as the sample diluent), and the resulting solution was added to the polystyrene plate MAXISORP (trademark) available from Thermo Fisher Scientific at 100 µL/well, and incubated at the room temperature for 1 hour. After the incubation, the solution was removed by an aspirator. ELISA Wash Solution available from Bethyl Laboratories (hereinafter referred to as the ELISA wash solution) was added to the plate at 200 µL/well, and the solution was removed by the aspirator immediately after the addition. The process of the addition and removal was repeated 5 times to wash the plate surface.

Then, a solution of a 100-mM Tris-HCl buffer (pH 8.0) and 0.5% by mass of the compound produced in Synthesis Example 4 dissolved was added to the plate at 200 μL/well, and incubated at 4° C. overnight. After the incubation, the solution was removed by the aspirator. The ELISA wash solution was added thereto at 200 μL/well, and the solution was removed by the aspirator immediately after the addition. The process of the addition and removal was repeated 5 times to wash the plate surface.

A treated plate for evaluating a protein adsorption-inhibiting effect, which had the base body (polystyrene plate) and had thereon a human albumin (protein) adsorption layer and a coating layer containing the protein adsorption inhibitor using the compound of Synthesis Example 4 as the active ingredient, was produced in this manner. This plate is hereinafter referred to as the treated plate.

[Evaluation of Protein Adsorption-Inhibiting Effect]

Human Reference Serum available from Bethyl Laboratories was diluted with the sample diluent. Thus obtained solutions had albumin concentrations of 400, 200, 100, 50, 25, 12.5, 6.25, 3.125, and 1.56 ng/mL respectively. Each solution having the concentration was added at 100 μL/well to each of the above treated plate and the untreated plate, and was incubated at the room temperature for 1 hour. After the incubation, the solution was removed by the aspirator. The ELISA wash solution was added thereto at 200 μL/well, and the solution was removed by the aspirator immediately after the addition. The process of the addition and removal was repeated 5 times to wash the plate surface.

Next, HRP Conjugated Human Albumin Detection Antibody available from Bethyl Laboratories was 70000-fold diluted with the sample diluent, added to the plate at 100 μL/well, and incubated at the room temperature for 1 hour. After the incubation, the solution was removed by the aspirator. The ELISA wash solution was added thereto at 200 μL/well, and the solution was removed by the aspirator immediately after the addition. The process of the addition and removal was repeated 5 times to wash the plate surface.

Then, TMB Microwell Peroxidase Substrate available from KPL was added to the plate at 100 μL/well, and incubated at the room temperature for 10 minutes. A 1-M sulfuric acid was added thereto at 50 μL/well to stop the reaction, and the absorbance was measured with respect to a light having a wavelength of 450 nm by the microplate reader Spectra Max M3 available from Molecular Devices to detect the adsorbed protein (human albumin). A lower absorbance means that the protein adsorption was inhibited more highly. The evaluation results are shown in Table 2 and FIG. 1.

TABLE 2

| Human albumin concentration (ng/mL) | Absorbance (at 450 nm) | |
| --- | --- | --- |
| | Treated plate (Example 2) | Untreated plate |
| 400.000 | 2.89 | 3.21 |
| 200.000 | 2.71 | 3.34 |
| 100.000 | 2.46 | 3.09 |
| 50.000 | 2.12 | 2.92 |
| 25.000 | 1.62 | 2.95 |
| 12.500 | 1.02 | 2.81 |
| 6.250 | 0.56 | 3.01 |
| 3.125 | 0.31 | 2.74 |
| 1.560 | 0.17 | 2.83 |

As is clear from Table 2 and FIG. 1, the treated plate, which was prepared by adsorbing the protein (human albumin) to the reaction vessel (plate) and by treating the plate with the protein adsorption inhibitor solution according to the present invention, was capable of more highly inhibiting the adsorption of the protein other than the detection subject, particularly at low concentrations, as compared with the untreated reaction vessel.

Example 3-1

Examples 3-1-1 to 3-1-4

<Preparation of Protein Adsorption Inhibitor Solution>

The compound of Synthesis Example 1 was dissolved in the D-PBS to prepare a protein adsorption inhibitor solution having a concentration of 0.5% to 5% by mass according to each of Examples 3-1-1 to 3-1-4.

<Production of Coating Layer-Formed Base Body Having Coating Layer Containing Protein Adsorption Inhibitor on Surface of Base Body>

The protein adsorption inhibitor solution was added to the polystyrene plate MAXISORP (trademark) available from Thermo Fisher Scientific at 200 μL/well, and left at the room temperature for 2 hours. Then, the solution was completely removed by the aspirator. The plate was dried for 24 hours to produce a base body with a coating layer formed on a surface, the coating layer containing a protein adsorption inhibitor using the compound of Synthesis Example 1 as an active ingredient. Such a product having a base body and a coating layer formed thereon is referred to as a coating layer-formed base body.

<Evaluation of Protein Adsorption-Inhibiting Effect>

The protein adsorption-inhibiting effect of the coating layer-formed base body was evaluated as follows.

POD-IgG available from Biorad was 20000-fold diluted with the D-PBS, and the resultant POD-IgG solution was added to the coating layer-formed base body at 100 μL/well, and left at the room temperature for 1 hour. Then, the POD-IgG solution was completely removed by the aspirator. A phosphate buffer containing 0.05% by mass of Tween 20 was added thereto at 200 μL/well, and the solution was removed by the aspirator immediately after the addition. The process of the addition and removal was repeated 5 times to wash the plate surface. After the washing, TIM Microwell Peroxidase Substrate available from KPL was added thereto at 100 μL/well, and reacted at the room temperature for 7 minutes. A 1-mol/L sulfuric acid solution was added thereto at 50 μL/well to stop the chromogenic reaction, and the absorbance was measured with respect to a light having a wavelength of 450 nm by the microplate reader Spectra Max M3 available from Molecular Devices to detect the adsorbed protein. A lower absorbance means that the protein adsorption was inhibited more highly.

In the evaluation of the protein adsorpt inhibiting effect, the absorbance of an example using a conventional bovine serum albumin was used as a reference. When a coating layer-formed base body exhibited an absorbance similar to that of the bovine serum albumin, the body was judged to have a sufficient effect. The evaluation results are shown in Table 3.

Example 3-2

Examples 3-2-1 to 3-2-6

Protein adsorption inhibitor solutions were prepared and coating layer-formed base bodies were produced in the same manner as Example 3-1 except that the compound produced in Synthesis Example 2 was used instead of the compound produced in Synthesis Example 1 at the concentrations shown in Table 3 respectively. The protein adsorption-inhibiting effects of the bodies were evaluated in the same manner as Example 3-1. The results are shown in Table 3.

Example 3-3

Examples 3-3-1 to 3-3-6

Protein adsorption inhibitor solutions were prepared and coating layer-formed base bodies were produced in the same manner as Example 3-1 except that the compound produced in Synthesis Example 3 was used instead of the compound produced in Synthesis Example 1 at the concentrations shown in Table 3 respectively. The protein adsorption-inhibiting effects of the bodies were evaluated in the same manner as Example 3-1. The results are shown in Table 3.

Example 3-4

Examples 3-4-1 to 3-4-6

Protein adsorption inhibitor solutions were prepared and coating layer-formed base bodies were produced in the same manner as Example 3-i except that the compound produced in Synthesis Example 4 was used instead of the compound produced in Synthesis Example 1 at the concentrations shown in Table 3 respectively. The protein adsorption-inhibiting effects of the bodies were evaluated in the same manner as Example 3-1. The results are shown in Table 3.

Comparative Example 3-1

The protein adsorption-inhibiting effect of Comparative Example 3-1 was evaluated in the same manner as Example 3-1 except that the protein adsorption inhibitor was not used and only the D-PBS was used. Incidentally, the body used in the evaluation in Comparative Example 3-1 was substantially the same as the untreated body. The result is shown in Table 3.

Comparative Example 3-2

The protein adsorption-inhibiting effect of Comparative Example 3-2 was evaluated in the same manner as Example 3-1 except that the BSA was used as a protein adsorption inhibitor to prepare a protein adsorption inhibitor solution having a concentration of 2% by mass. The result is shown in Table 3.

Comparative Example 3-3

The protein adsorption-inhibiting effect of Comparative Example 3-3 was evaluated in the same manner as Example 3-1 except that the compound produced in Comparative Synthesis Example 1 was used instead of the compound produced in Synthesis Example 1 at the concentration of 5% by mass. The result is shown in Table 3.

Comparative Example 3-4

The protein adsorption-inhibiting effect of Comparative Example 3-4 was evaluated in the same manner as Example 3-1 except that the compound produced in Comparative Synthesis Example 2 was used instead of the compound produced in Synthesis Example 1 at the concentration of 5% by mass. The result is shown in Table 3.

Comparative Example 3-5

The protein adsorption-inhibiting effect of Comparative Example 3-5 was evaluated in the same manner as Example 3-1 except that the compound produced in Comparative Synthesis Example 3 was used instead of the compound produced in Synthesis Example 1 at the concentration of 5% by mass. The result is shown in Table 3.

TABLE 3

| | Protein adsorption inhibitor | | |
|---|---|---|---|
| | Syn. Ex. | Concentration (% by mass)*[1] | Absorbance (at 450 nm) |
| Ex. 3-1  -1 | 1 | 5.00 | 0.048 |
| -2 | | 2.00 | 0.047 |
| -3 | | 1.00 | 0.080 |
| -4 | | 0.50 | 0.193 |
| Ex. 3-2  -1 | 2 | 5.00 | 0.046 |
| -2 | | 2.00 | 0.048 |
| -3 | | 1.00 | 0.051 |
| -4 | | 0.50 | 0.054 |
| -5 | | 0.20 | 0.068 |
| -6 | | 0.10 | 0.302 |
| Ex. 3-3  -1 | 3 | 5.00 | 0.046 |
| -2 | | 2.00 | 0.046 |
| -3 | | 1.00 | 0.047 |
| -4 | | 0.50 | 0.044 |
| -5 | | 0.20 | 0.046 |
| -6 | | 0.10 | 0.047 |
| Ex. 3-4  -1 | 4 | 5.00 | 0.043 |
| -2 | | 2.00 | 0.047 |
| -3 | | 1.00 | 0.046 |
| -4 | | 0.50 | 0.047 |
| -5 | | 0.20 | 0.047 |
| -6 | | 0.10 | 0.049 |
| Comp. Ex. 3-1 | — | — | 2.421 |
| Comp. Ex. 3-2 | BSA*[2] | 2.00 | 0.048 |
| Comp. Ex. 3-3 | Comp. Syn. Ex. 1 | 5.00 | 2.244 |
| Comp. Ex. 3-4 | Comp. Syn. Ex. 2 | 5.00 | 1.626 |
| Comp. Ex. 3-5 | Comp. Syn. Ex. 3 | 5.00 | 0.169 |

*[1]Concentration in protein adsorption inhibitor solution
*[2]Bovine serum albumin The BSA used in Comparative Example 3-2 is a common biological protein having an excellent protein adsorption-inhibiting function. Each coating layer-formed base body having the coating layer containing the protein adsorption inhibitor of the present invention utilized the compound represented by Formula (1) as the active ingredient, and thereby exhibited a protein adsorption-inhibiting function similar to that of the BSA. In contrast, Comparative Examples other than Comparative Example 3-2 exhibited poor protein adsorption-inhibiting functions.

What is claimed is:
1. A method for inhibiting adsorption of a protein to a base body, comprising treating a surface of the base body with a protein adsorption inhibitor to form a coating layer,
wherein the protein adsorption inhibitor comprises, as an active ingredient, a compound of following Formula (1):

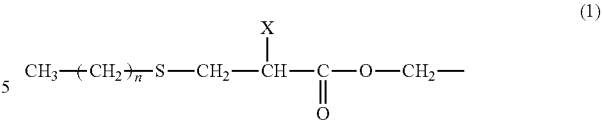

-continued $$-CH_2-O-\underset{\underset{O}{\|}}{\overset{\overset{O^-}{|}}{P}}-O-CH_2-CH_2-\underset{\underset{CH_3}{|}}{\overset{\overset{CH_3}{|}}{N^+}}-CH_3$$

wherein X is a hydrogen atom or a methyl group and n is an integer of 9 to 15.

2. The method according to claim 1, further comprising drying the surface that is treated with the protein adsorption inhibitor, to form the coating layer.

\* \* \* \* \*